United States Patent [19]

Jungmann, deceased

[11] 4,275,718
[45] Jun. 30, 1981

[54] PELVIC DEVICE

[75] Inventor: Martin Jungmann, deceased, late of Rangeley, Me., by Gertrude Jungmann, heir

[73] Assignee: Institute for Gravitational Strain Pathology, Inc., New York, N.Y.

[21] Appl. No.: 63,048

[22] Filed: Aug. 2, 1979

[51] Int. Cl.³ .............................................. A61F 5/24
[52] U.S. Cl. ...................................... 128/95; 128/103; 128/104; 128/123
[58] Field of Search ................... 128/95, 96, 103, 104, 128/105, 111, 122, 124, 106

[56] References Cited

U.S. PATENT DOCUMENTS

| 522,967 | 7/1894 | Chapman et al. | 128/99 |
| 2,051,921 | 8/1936 | Turner | 128/103 |
| 2,203,037 | 6/1940 | Walter | 128/122 |
| 3,021,838 | 2/1962 | Fine | 128/96 |
| 3,032,034 | 5/1962 | Jungmann | 128/111 |
| 3,532,090 | 10/1970 | Ward | 128/95 |

FOREIGN PATENT DOCUMENTS 2515103 10/1976 Fed. Rep. of Germany ............. 128/95

Primary Examiner—Robert W. Michell
Assistant Examiner—J. L. Kruter
Attorney, Agent, or Firm—Friedman, Goodman & Teitelbaum

[57] ABSTRACT

A pelvic device which includes a pair of pads, one pad of which can be located in opposed relationship to the pubic bone and the other pad in opposed relationship to the lower sacrum. Each pad is rotatably connected to a connecting bar. Each connecting bar respectively interconnects the lateral ends of a pair of convexly curved metal spring members to provide a closed loop which can encircle the body without touching any soft tissue, pressure being exerted only on pubic bone in front and lower sacrum. One of the connecting bars is hingedly connected to its associated pair of lateral ends while the other connecting bar is rigidly connected to one of its associated lateral ends, and includes a latch interconnecting it to the other of its associated lateral ends. Each pad can be controllably inflated to regulate its outer contour thereby controlling the amount of pressure that the device can exert onto the wearer of the device.

11 Claims, 8 Drawing Figures

PELVIC DEVICE

BACKGROUND OF THE INVENTION

This invention relates to a pelvic device, and more particularly to a device which can exert resilient pressure against various body portions to thereby relieve the effects of gravitational strain.

In U.S. Pat. No. 2,320,183 granted to the applicant, Martin Jungmann, there is disclosed a device which includes opposed pads applicable to the pubic bone and the lower sacrum. By application of these pads, pressure can be exerted on the body to overcome the adverse effects of gravitational forces on the body frame in its normal upright position. Such device was found useful in treating numerous types of conditions such as backache, sacroiliac disturbances, lumbago, fatigue, and the like, caused by gravitational strain.

In U.S. Pat. No. 3,032,034, also granted to the applicant, Martin Jungmann, there is disclosed an improved device which permits more precise control of the pressure applied to the pubic bone and lower sacrum. The improved device includes the pads as part of a resilient body encircling system. The pads are included within body encircling members formed of metallic spring material and each of the pads are connected to the body encircling members by means of springs. One pad is used for adjustable resiliency by means of varying the spacing between bowed spring members connecting the pad to the body encircling members.

While such pelvic devices have been found useful in redressing the relative positions of the pubic and lower sacrum to counteract gravitational strain, it has been found that greater flexibility is needed to individualize the device for each wearer to thereby conform the shape and pressure of the device of the wearer's configuration. In many situations, it is not only the amount of resiliency which is important, but the shape of the users bones may vary, and therefore, flexibility is needed to regulate the pad shape to permit conformity of the pad to the bones.

Additionally, the encircling members must be able to take and hold a specific set in order to assure a proper fit around the wearer. The encircling members must be able to flex at a varied rate and exert a specific adjusted pressure onto the wearer. Furthermore, the connecting members between the encircling members must have a suitable amount of resiliency to "give" as the user carries out daily body movements including bending, lifting of objects, twisting and even breathing. Such resiliency and flexure of the body encircling members and the connecting bars are of crucial importance, and the materials utilized in the prior patents have not proved sufficiently suitable for the results desired.

SUMMARY OF THE INVENTION

It is accordingly an object of the present invention to provide an improved pelvic device which can be utilized to overcome the adverse effects of gravitational forces on the body frame in its normal upright position.

Still a further object of the present invention is to provide a pelvic device comprising a pair of pad members which can be positioned in opposed relationship to the pubic bone and the lower sacrum, and which can provide the appropriate shape and fit to conform to the wearer.

Yet a further object of the present invention is to provide a pelvic device which includes a pair of opposed pads as part of a body encircling system, and wherein the device exhibits a proper amount of flexure to accommodate itself to the wearer's movements.

A further object of the present invention is to provide a pelvic device comprising a pair of pad members disposed within a body encircling system of spring members, wherein the body encircling system can take and hold a specific set in order to assure a proper fit around the person wearing the device.

Another object of the present invention is to provide a pelvic device having a pair of pad members included within a body encircling system, and which provides better fit and adjustment of its shape and pressure onto the body portions, and which also produces greater flexure and resiliency in order to provide more improved results.

Still another object of the present invention is to provide a pelvic device which is simple in construction, easier to apply, and has better control than prior art devices.

Briefly, the present invention provides for a pelvic device having a pair of pad members respectively adapted to be located in opposed relationship to the pubic bone and the lower sacrum. A pair of convexly curved metal spring members encircle the body by means of a pair of metal connecting flat spring-bars respectively interconnecting the lateral ends of the curved members. Hinges connect the ends of one connecting spring-bar to the adjacent lateral ends of the curved members interconnected thereby. A latch is provided for detachably connecting one end of the other connecting bar with an adjacent lateral end of one curved member interconnected thereby, and the opposite end of the other connecting bar is rigidly connected to an adjacent lateral end of the other curved member interconnected thereby. Each pad member is rotatably coupled to a respective one of the metal connecting spring-bars. Each of the pad members can be inflated with varying amounts of air to thereby control the outer contour of the pad member.

In a preferred embodiment of the invention, the connecting bars are formed of special spring steel, commonly known as T-410, which is tempered and annealed to E-74. This steel provides improved fit and better operation of the device, where it provides the material with a suitable amount of flexure, thus permitting body movements by the wearer.

In an embodiment of the invention, the curved metal spring members which encircle the body are made of aluminum 7075 hardened to T-6. This aluminum provides improved results by permitting the material to take and hold a specific set, thereby assuring proper fit around the wearer. At the same time, the aluminum permits flexure at a continued rate, and exerts a specific adjusted pressure onto the wearer.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which.

In the various figures of the drawing, like reference characters designate like parts.

DETAILED DESCRIPTION OF THE PREFERRED EMBODIMENT

The pelvic device of the present invention comprises a pair of opposed pads which form elements of a closed loop system of resilient spring members adapted to encircle the pelvic region of the wearer, in order to mount the pads in pressure applying relationship on the pubic bone and the lower sacrum without touching any soft tissue parts of the body.

Figure 1:
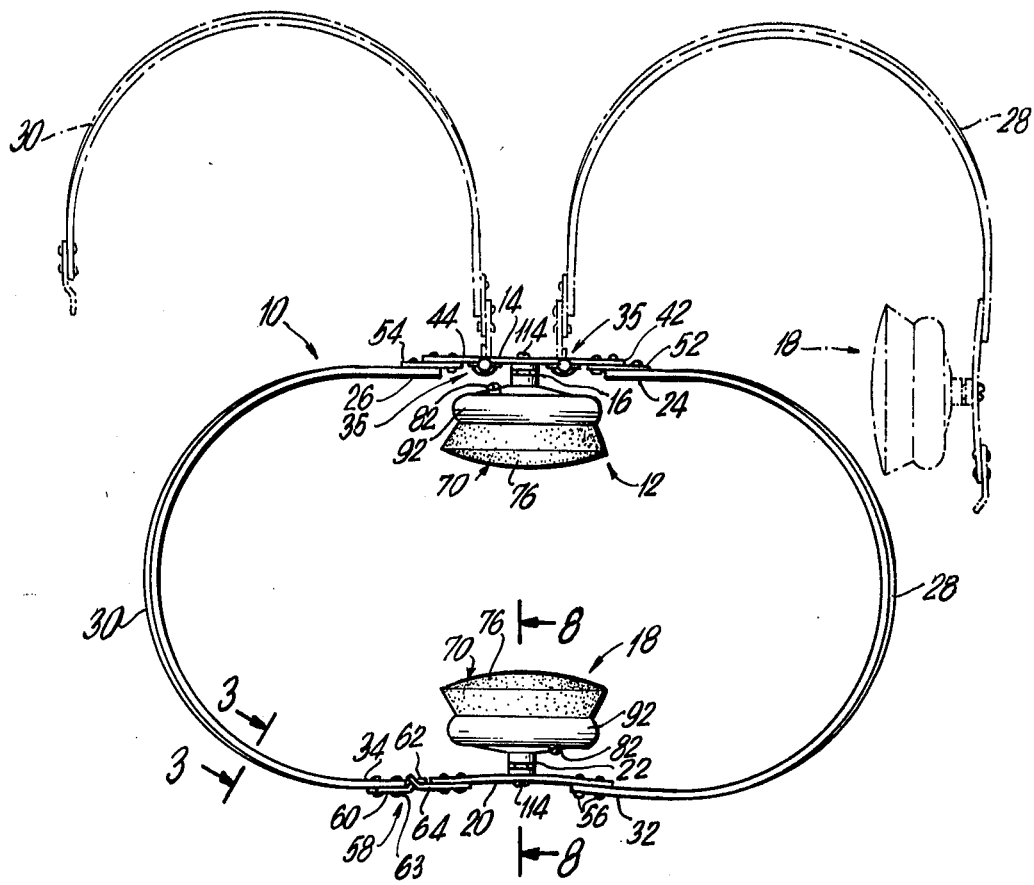
FIG. 1 is a top plan view of the pelvic device, in accordance with the present invention, showing an open position thereof in phantom lines.

As shown in FIG. 1, the device of the present invention, shown generally at 10, includes a first pad member 12 rotatably coupled onto the inner surface of a substantially flat connecting bar 14 formed of flat spring steel, by means of the rotary joint coupling 16. A second pad member 18, opposed from the first pad member 12 is rotatably mounted on the inner surface of another substantially flat connecting bar 20 also formed of flat spring steel, by means of a similar rotary joint coupling 22. Connecting bar 14 is positioned between the lateral ends 24, 26 of curved resilient spring members 28, 30, respectively. The other laterally adjacent ends 32, 34, of the curved spring members 28, 30, respectively, are interconnected by means of the other connecting bar 20.

Figure 5:
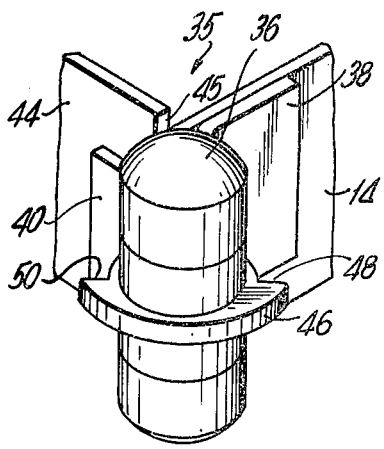
FIG. 5 is an enlarged perspective view of one of the hinged interconnections between a connecting bar and a body encircling member.
Figure 6:
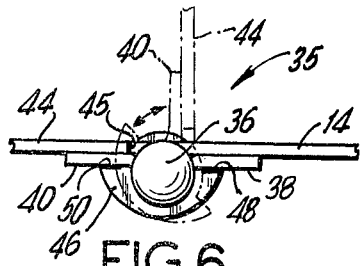
FIG. 6 is a reduced top view of the hinge shown in FIG. 5.

The interconnections between the connecting bar 14 and its laterally adjacent ends, are by means of hinge connections 35. As shown more specifically in FIG. 5 and 6 which shows the left hinge of FIG. 1, each hinge 35 comprises a hinge pin 36 for connecting together an upper hinge plate 38 and a lower hinge plate 40 which have aligned looped hinge portions formed by one of the plates being a bent around portion of the opposing brackets 42, 44, and the other plate being a bent around portion of the bar 14 therebetween. A circular abutment 46, having shoulders 48, 50, is mounted onto the hinge pin and provides stops for limiting the rotational movement of the circular curved members. The 180° abutment 46 limits the inward swing of the curved members 28, 30 whereby the shoulders 48, 50 engage the plates 38, 40 to stop the bar 14 and brackets 42, 44 when they are in straight alignment with each other as shown in FIGS. 1 and 6. The rotational movement is shown in FIGS. 1 and 6 by means of the phantom lines which show the curved members in their open position, being limited to 90° by the engagement of the edge 45 of the brackets 44 and 42 against the outside surface of the bar 14, as shown in FIG. 6, where in this open position, the edges of the bar 14 also engage the outside surface of the brackets 42 and 44. As shown in FIG. 1, the brackets 42, 44, are also coupled to the laterally adjacent ends 24, 26 of the curved members 28, 30 by means of the additional plates 52, 54. The interconnection between the various plates is achieved by means of rivets. However, screw fasteners or other types of connecting means could similarly be utilized. Plates 52 and 54 are extension plates. They allow adjustment of the circumference measurement of the device as deemed necessary by physician. They may be deleted if not needed.

Figure 4:
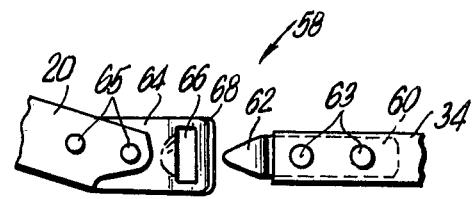
FIG. 4 is a fragmented rear elevational view of the latch portion, as shown from the inside of the device.

The connecting bar 20 has one end thereof rigidly connected to the laterally adjacent end 32 of the curved member 28. Such connection is shown by way of example, by means of the rivets 56. The other end of the connecting bar 20 is detachably connected to the end 34 of the curved member 30 by means of the latch arrangement shown generally at 58. As is shown more specifically in FIG. 4, the latch arrangement 58 includes an arm 60 having an inwardly offset tongue portion 62 extending therefrom. The arm 60 is securely connected to the end 34 of the curved member 30 by fastener means 63 such as rivets. Connected to the end of the connecting bar 20, by fastener means 65 such as rivets, is a receiving arm 64 having a rectangular opening or slot 66 in its end 68. The end 68 is also inwardly offset to receive the offset tongue 62. The latch arrangement 58 is such that the resiliency of the curved members 28, 30 presses or forces the receiving arm 64 against the back of the tongue 62 to effectively lock the tongue in the receiving rectangular opening 66. In order to release the latch, the receiving arm 64 is pushed inwardly to remove the pressure and release the tongue 62 from the rectangular opening 66.

Figure 7:
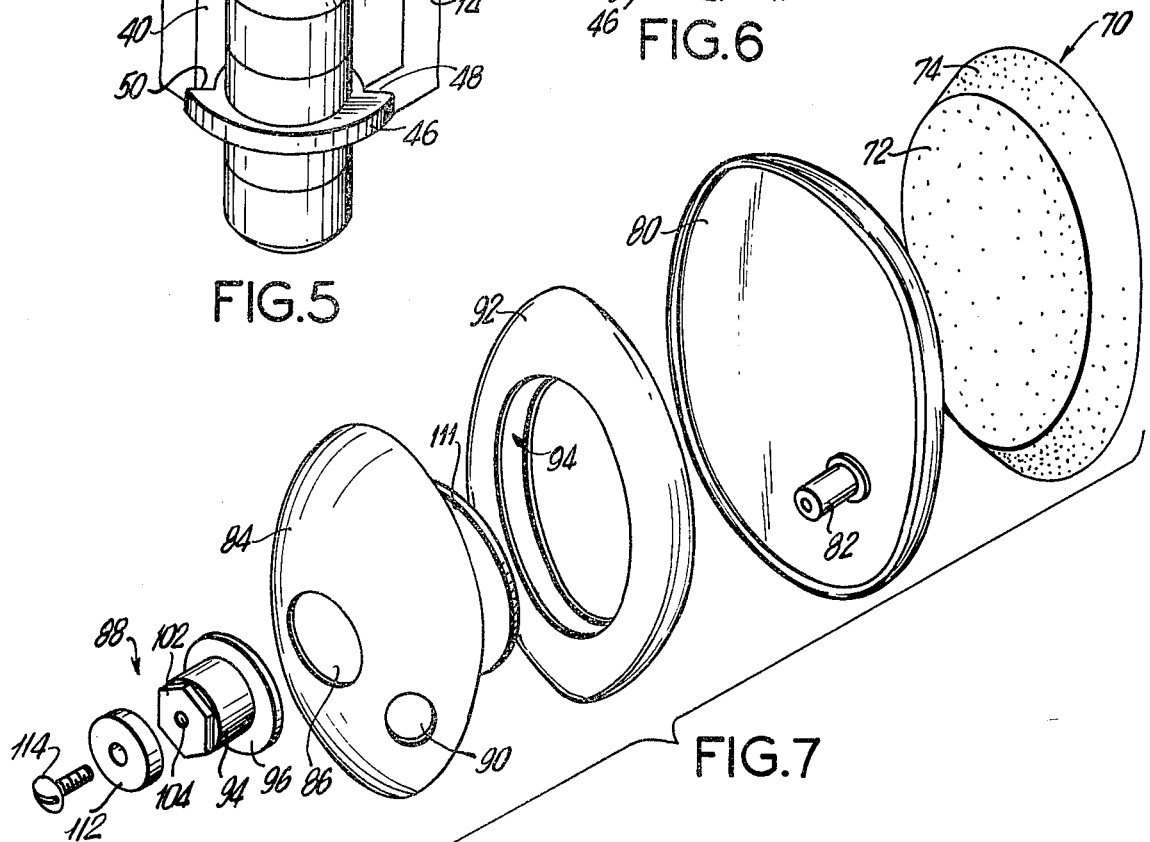
FIG. 7 is an enlarged exploded perspective view of the components of the pad including the coupling arrangement for connecting the pad to the connecting bar.
Figure 8:
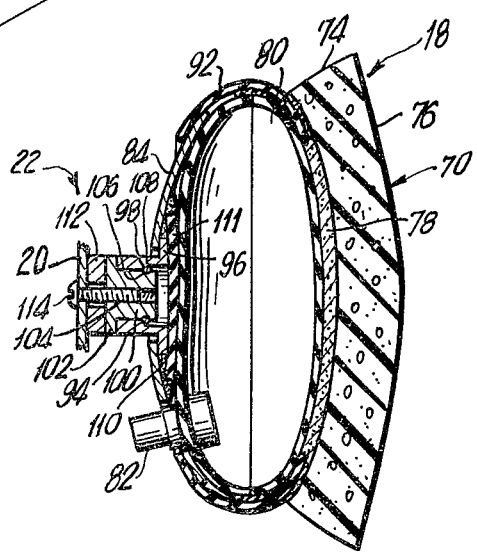
FIG. 8 is an enlarged view taken through an assembled pad member along line 8—8 of FIG. 1.

Referring now to the exploded view of the components of each pad member and the coupling arrangement therefor as shown in FIG. 7, and the cross sectional view of the pad member 18 and the joint coupling 22 shown in FIG. 8, each of the pad members 12, 18 is shown to include a resilient foam portion 70 formed with an arcuate wall 72 on one side thereof, frustroconical sidewalls 74, and a spherical wall 76 on the opposite side thereof. The arcuate wall 72 is secured, by means of adhesive material 78, to an outer surface of an oval shaped bladder 80 formed of a flexible inflatable material, such as rubber or vinyl. A conventional filling valve 82 is securely connected to an opening in the opposite surface of the bladder 80 to permit inflation of the bladder.

Against the opposite surface of the bladder, a support member 84 is positioned, being formed of rigid material such as steel, and being in the shape of a clam shell. A central opening 86 is provided in the support member for receiving a rotary coupling joint shown generally at 88, which is either the rotary joint coupling 16 or 22 when mounted on its associated connecting bar 14 or 20. An offset opening 90 is also provided in the support member through which the filling valve 82 can extend. The support member 84 is held against the bladder 80 by means of a flexible annular retaining ring 92 having an open interior 94 therein for receiving the edges of the support member and the bladder.

The rotary coupling joint 88 is formed of a first member having a cylindrical hollow body portion 94 with an outwardly extending flanged base 96. A shoulder 98 is formed internally of the hollow body portion 94. By way of example, the shoulder can be formed by having a two diameter inner surface with the interface between the two diameters providing the shoulder. A second member having a cylindrical body portion 100 is inserted within the larger hollow body portion 94, and terminates in an outwardly extending flanged head 102 formed in the shape of a hexagonal head. A threaded bore 104 is formed through the hexagonal head 102 and the body portion 100. A circumferential groove 106 is formed about the exterior of the cylindrical body portion 100 and is positionable proximate the shoulder portion 98. With the cylindrical body portion 100 inserted within the outer body portion 100 inserted within the outer body portion 94, a retaining ring 108 is placed in the groove 106. The retaining ring 108 is held by the groove and prevents axial movement of the inner cylindrical portion 100 from the outer cylindrical portion 94 by means of the retaining shoulder 98. However, the two body portions 94, 100 can rotate relative to each other.

The body portion 94 and the body portion 100 connected thereto are inserted through the opening 86 in the clam shell support member 84 so that the base flange 96, which is larger than the opening 86, provides connection therebetween. The base flange 96 is securely held in place by means of adhesive material 110 and disc diaphragm 111. The hexagonal head 102 is utilized for fastening the pad members 12, 18 to the connecting bars 14, 20, respectively. A collar 112 is placed over the hexagonal head 102 on the inner sides of connecting bars 14, 20. A screw 114 is inserted through an opening provided in each of the connecting bars and threaded into the threaded bore 104 in the hexagonal head, as indicated in FIG. 8 showing the assembled pad member 18 connected to the connecting bar 20. The hexagonal head 102 can be held by a tool, such as a wrench, while tightening the screw therein. Use of collar 112 is optional as deemed necessary by physician to attain proper fit. Collar 112 comes in a multitude of thicknesses from ⅛" to ⅜".

With the pads 12, 18 assembled on the connecting bars 14, 20, the pads can be rotated with respect to the connecting bars to adjust the pads for proper positioning thereof. Also, the amount of pressure as well as the contour of the pad can be appropriately regulated by controlling the amount of pressure in the bladder which is disposed against the foam pad, where the pressure may be increased or decreased by inserting more air into or by taking a selected amount of air out of the bladder 80 through the valve 82.

The connecting bars 14, 20 is preferably formed of steel. A crucial part of the device is to ensure a proper fit, where it is necessary for the device to be worn throughout continued movement of the wearer during normal daily activities. As a result, there is repeated bending and torisonal strain applied to the connecting bars during bending, rotation of the body, stretching and even breathing. Sufficient flexure or "give" must be provided in these connecting bars to accept such movement. It has been found that steel T-410 tempered and annealed to E-74 is especially suited for such purposes. This steel gives the proper amount of flexure, thereby giving the wearer the benefits of the device.

Figure 3:
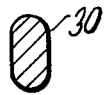
FIG. 3 is a sectional view taken through one body encircling member along line 3—3 of FIG. 1.

The curved spring members 28, 30 typically have an elliptical shape, as shown in FIG. 3. These members must also be fabricated from a material which permits modification of the curvature thereof. During continued use of the device, the contour of the device must be changed, usually by means of suitable tools, to modify the curvature or the inclination of the cross sectional portions thereof with respect to the vertical. In this way the device can be progressively accommodated to the actual body contours of the wearer and at the same time permit proper adjustment of the pressures required for proper redressment. Accordingly, the curved members must accept repeated bending and torsional strains and must retain a selected shape once set.

It has been found that a most suitable material for such curved members 28, 30 is aluminum 7075 hardened to T-6. This metal is most uniquely accommodating to the specific needs of the present device. It can take and hold a specific set to assure proper fit around the person wearing it. It is also able to flex at a very specific rate and exert a specific, adjusted pressure.

Of crucial importance is the ability in the present device to modify the pressure directly between the pad and the bone as well as the particular contour or shape of the pad to accommodate to the bone. It is important that the pads "hug" the bones. The shape, size, and contour of the bones vary between individuals, and even with the same individual, continued use causes changes in the position of such bones. The present pads 12, 18 are extremely convenient for use in such modification since each pad can easily rotate, and accordingly the angle of application of the pad to the bone can be adjusted. Also, by controlling the amount of air within the bladder, the pressure and contour of the pad can be selectively determined to accommodate the user's bones.

Figure 2:
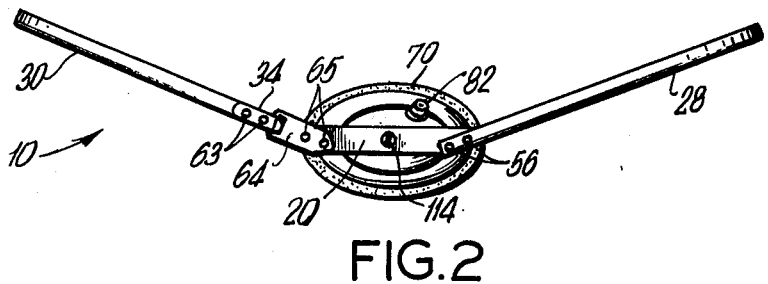
FIG. 2 is a front elevational view of the device showing the interconnection between a pad, a connecting bar, and laterally adjacent ends of the body encircling members.

An additional feature of the invention is the particular shape of the entire device. As can best best be seen in FIG. 2, the curved members diverge angularly from the plane of the connecting bar. It is therefore appreciated that the entire device does not lie in a common plane but the curved members are angularly positioned with respect to the connecting bars.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. In a pelvic device having a pair of pad members respectively adapted to be located in opposed relationship to a pubic bone and a lower sacrum of a wearer's body, a pair of curved spring members for encircling the body, a pair of connecting bars respectively interconnecting lateral ends of said curved members, latch means for detachably connecting one end of one of said connecting bars to an associated one of said lateral ends of one of said curved members on one side of said device, and coupling means rotatably connecting each of said pad members to an associated one of said connecting bars respectively, an improvement comprising:

each pad member including inflating means for individual inflation thereof to regulate its respective outer contour;

each of said pad members including an inflatable bladder;

a resilient pad being mounted onto one side of each of said bladders, and an associated supporting member being coupled to an opposite side of each of said bladders;

each of said coupling means being connected to its said associated supporting member;

each of said coupling means extending through a central opening provided in its said associated supporting member; and each of said inflating means including a filling valve extending from said bladder through an offset opening provided in its said associated supporting member for access thereto.

2. A pelvic device as in claim 1 and further comprising a flexible ring member clamping each said bladder to its said associated supporting member.

3. A pelvic device as in claim 1, wherein each said coupling means includes a rotary joint coupling.

4. A pelvic device as in claim 1, wherein said curved spring members are mechanically bendable metal to take and hold a specific set, and wherein said connecting bars are of flexible resilient metal material.

5. A pelvic device as in claim 4, wherein said curved metal spring members are of aluminum 7075 hardened to T-6.

6. A pelvic device as in claim 4, wherein said connecting bars are of T-410 spring steel which is tempered and annealed to E-74.

7. A pelvic device as in claim 1, wherein said curved spring members respectively diverge from a plane containing said connecting bars.

8. In a pelvic device according to claim 1 further including a pair of hinge means for connecting opposite ends of the other connecting bar to the opposite two adjacent ends of said curved members on the other side of said device, a further improvement comprising:

stop means for limiting rotational movement of each of said curved members about an associated one of said hinge means to substantially 90° with respect to said other connecting bar.

9. A pelvic device as in claim 8, wherein said stop means includes an abutment mounted on each of said hinge means, each of said abutments including spaced apart shoulders, one of said shoulders being engageable with an associated portion of said other connecting bar, and the other of said shoulders being engageable with an associated bracket portion of each of said opposite two adjacent ends of said curved members.

10. A pelvic device comprising:

a pair of pad members respectively adapted to be located in opposed relationship to a pubic bone and a lower sacrum of a wearer's body, a pair of curved metal spring members for encircling the body, a pair of metal connecting bars respectively interconnecting lateral ends of said curved members, hinge means for connecting opposite ends of one of said connecting bars to two adjacent lateral ends of said curved members on one side of said device, latch means for detachably connecting one end of the other connecting bar to the other lateral end of one of said curved members on the other side of said device, securing means for rigidly connecting an opposite end of said other connecting bar to the other lateral end of the other one of said curved members on said other side of said device, coupling means rotatably connecting each of said pad members to an associated one of the metal connecting bars respectively, each pad member including inflating means for individual inflation thereof to regulate its respective outer contour, each of said pad members including an inflatable bladder, a resilient pad mounted onto one side of said bladder, and a supporting member coupled to an opposite side of said bladder, said coupling means being connected to said supporting member, and said bladder being substantially of oval shape, and said supporting member being a metal member of clam shell configuration having a central opening through which said coupling means extends and an offset opening, said inflating means including a filling valve extending from said bladder through said offset opening of said supporting member.

11. A pelvic device comprising:

a pair of pad members respectively adapted to be located in opposed relationship to a pubic bone and a lower sacrum of a wearer's body, a pair of curved metal spring members for encircling the body, a pair of metal connecting bars respectively interconnecting lateral ends of said curved members, hinge means for connecting opposite ends of one of said connecting bars to two adjacent lateral ends of said curved members on one side of said device, latch means for detachably connecting one end of the other connecting bar to the other lateral end of one of said curved members on the other side of said device, securing means for rigidly connecting an opposite end of said other connecting bar to the other lateral end of the other one of said curved members on said other side of said device, coupling means rotatably connecting each of said pad members to an associated one of the metal connecting bars respectively, each pad member including inflating means for individual inflation thereof to regulate its respective outer contour, said coupling means including a rotary joint coupling, said rotary joint coupling comprising a first member having a cylindrical first body portion with an internal circular shoulder and having an outwardly flanged edge, a second member having a cylindrical second body portion extending into said first body portion and having an outwardly flanged edge overlying an opposite edge of said first body portion, a circular groove provided around a periphery of said second body portion proximate said circular shoulder of said first body portion, a retaining ring disposed in said groove for permitting relative rotation between said first and second members while preventing axial separation therebetween, a threaded bore provided in said outwardly flanged edge of said second body portion, a screw inserted through said associated connecting bar and threaded into said threaded bore, and adhesive means for rigidly securing said outwardly flanged edge of said first body portion to an associated one of said pad members.

* * * * *